(12) United States Patent
Hobbins et al.

(10) Patent No.: US 12,721,978 B2
(45) Date of Patent: Sep. 1, 2026

(54) CATHETER ASSEMBLY INCLUDING EXTRUDED POLYMER MATERIAL FOR STIFFNESS

(71) Applicant: MEDTRONIC VASCULAR, INC., Santa Rosa, CA (US)

(72) Inventors: David Hobbins, Galway (IE); Risa Egerter, Galway (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 560 days.

(21) Appl. No.: 17/653,786

(22) Filed: Mar. 7, 2022

(65) Prior Publication Data

US 2022/0323729 A1 Oct. 13, 2022

Related U.S. Application Data

(60) Provisional application No. 63/171,793, filed on Apr. 7, 2021.

(51) Int. Cl.
*A61M 25/10* (2013.01)
*A61M 25/01* (2006.01)

(52) U.S. Cl.
CPC . *A61M 25/1036* (2013.01); *A61M 2025/0183* (2013.01)

(58) Field of Classification Search
CPC ...... A61M 25/1036; A61M 2025/0183; A61M 25/10; A61M 25/0012; A61M 25/0052
See application file for complete search history.

(56) References Cited

U.S. PATENT DOCUMENTS 4,368,730 A 1/1983 Sharrock
5,217,482 A 6/1993 Keith
5,387,225 A * 2/1995 Euteneuer ........... A61M 25/104 604/96.01
5,499,973 A * 3/1996 Saab ................... A61M 25/104 604/264
5,947,940 A * 9/1999 Beisel ................. A61M 25/005 604/526
6,165,166 A * 12/2000 Samuelson ............. B29C 48/12 604/524
6,217,566 B1 4/2001 Ju
6,258,080 B1 * 7/2001 Samson ............ A61M 25/0053 604/525
6,960,188 B2 11/2005 Jörgensen
7,354,430 B2 4/2008 Pepin
(Continued)

FOREIGN PATENT DOCUMENTS

WO 95/05555 A1 2/1995

OTHER PUBLICATIONS

International Search Report and Written Opinion for corresponding Application No. PCT/IB2022/053226, Jun. 28, 2022, 13 pages, Rijswijk, Netherlands.

(Continued)

*Primary Examiner* — Andrew Restaino
(74) *Attorney, Agent, or Firm* — Stinson LLP

(57) ABSTRACT

The present disclosure provides a catheter that includes a catheter tube defining the guidewire lumen with the catheter tube including an extruded polymer material. Molecules of the extruded polymer material extend circumferentially around the catheter tube to stiffen the catheter tube for strengthening the catheter tube against radial compression forces.

11 Claims, 9 Drawing Sheets

(56) References Cited

U.S. PATENT DOCUMENTS

| | | | | |
|---|---|---|---|---|
| 8,465,462 | B2 | 6/2013 | Pepper | |
| 9,023,174 | B2 | 5/2015 | Simpson et al. | |
| 2003/0065352 | A1 | 4/2003 | Yang et al. | |
| 2004/0002728 | A1 | 1/2004 | Speck et al. | |
| 2007/0049903 | A1 | 3/2007 | Jansen | |
| 2007/0088296 | A1 | 4/2007 | Leeflang et al. | |
| 2008/0177227 | A1* | 7/2008 | Wilkins ............ | A61M 25/0045 604/103 |
| 2010/0004593 | A1 | 1/2010 | Gregorich et al. | |
| 2010/0087789 | A1 | 4/2010 | Leeflang et al. | |
| 2010/0121312 | A1* | 5/2010 | Gielenz ............... | A61M 25/005 604/524 |
| 2014/0236123 | A1 | 8/2014 | Birmingham | |
| 2015/0320971 | A1 | 11/2015 | Leeflan | |
| 2019/0009959 | A1 | 1/2019 | Dinh | |

OTHER PUBLICATIONS

U.S. Appl. No. 17/653,714.

* cited by examiner

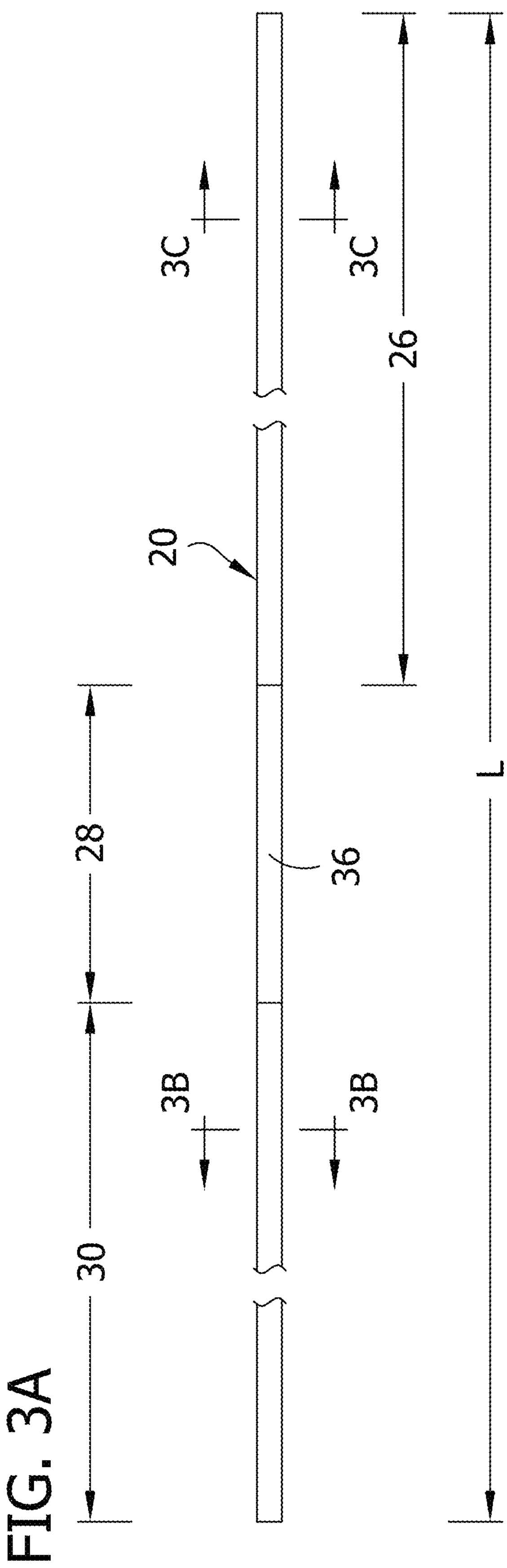
FIG. 3A
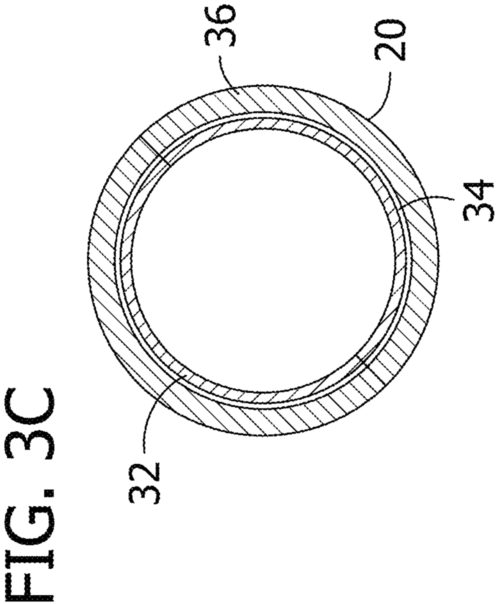
FIG. 3C
FIG. 3B

110

138

120

114

FIG. 4 harder polymer
softer polymer

A
B
C
D harder polymer
softer polymer

A

B

C

D

CATHETER ASSEMBLY INCLUDING EXTRUDED POLYMER MATERIAL FOR STIFFNESS

CROSS-REFERENCE TO RELATED APPLICATION

This application claims the benefit of U.S. Provisional Patent Application Ser. No. 63/171,793, filed on Apr. 7, 2021, the entire contents are hereby incorporated by reference.

FIELD

This disclosure is related generally to a catheter assembly, and more particularly to a balloon catheter assembly having a reinforced inflation lumen to resist pressure exerted on the inflation lumen when the balloon is inflated.

BACKGROUND

Balloons mounted on the distal ends of catheters or other medical devices are widely used in medical treatment. For example, a medical balloon may be used to widen a vessel into which the catheter is inserted, open a blocked vessel and/or deliver a medical device (e.g., a stent) to a treatment location inside a body, among other uses. In use, the balloon is delivered to a treatment location by inserting the balloon in an uninflated configuration through a body lumen (e.g., a blood vessel). Balloons can be inserted through a body lumen by tracking the uninflated balloon through an introducer sheath and/or along a guidewire. Once the uninflated balloon has reached the treatment location, fluid is delivered into the balloon, thereby expanding the outer circumference of the balloon (i.e., the balloon is inflated). After treatment, the balloon is deflated and withdrawn from the patient's body. In some cases, the balloon may later be re-introduced into the same or another body lumen of the patient.

SUMMARY

In one aspect, the present disclosure provides a catheter that includes a catheter tube defining the guidewire lumen with the catheter tube including an extruded polymer material. Molecules of the extruded polymer material extend circumferentially around the catheter tube to stiffen the catheter tube for strengthening the catheter tube against radial compression forces.

In another aspect, the present disclosure provides a method of making a catheter. The method includes the steps of extruding a polymer material such that molecules of the extruded polymer material extend axially along the polymer material and wrapping the extruded polymer material around a mandrel to form a catheter tube whereby the molecules of the polymer material extend circumferentially around the catheter tube.

BRIEF DESCRIPTION OF THE DRAWINGS

FIG. 3A is a side elevation of an inner inflation tube of the balloon catheter;

FIG. 3B is a cross-section of the inner inflation tube through line 3B-3B in FIG. 3A;

FIG. 3C is cross-section of the inner inflation tube through line 3C-3C in FIG. 3A;

FIG. 4 is a fragmentary perspective of a balloon catheter of another embodiment;

Corresponding reference characters indicate corresponding parts throughout the drawings.

DETAILED DESCRIPTION OF THE DISCLOSURE

Figure 1:
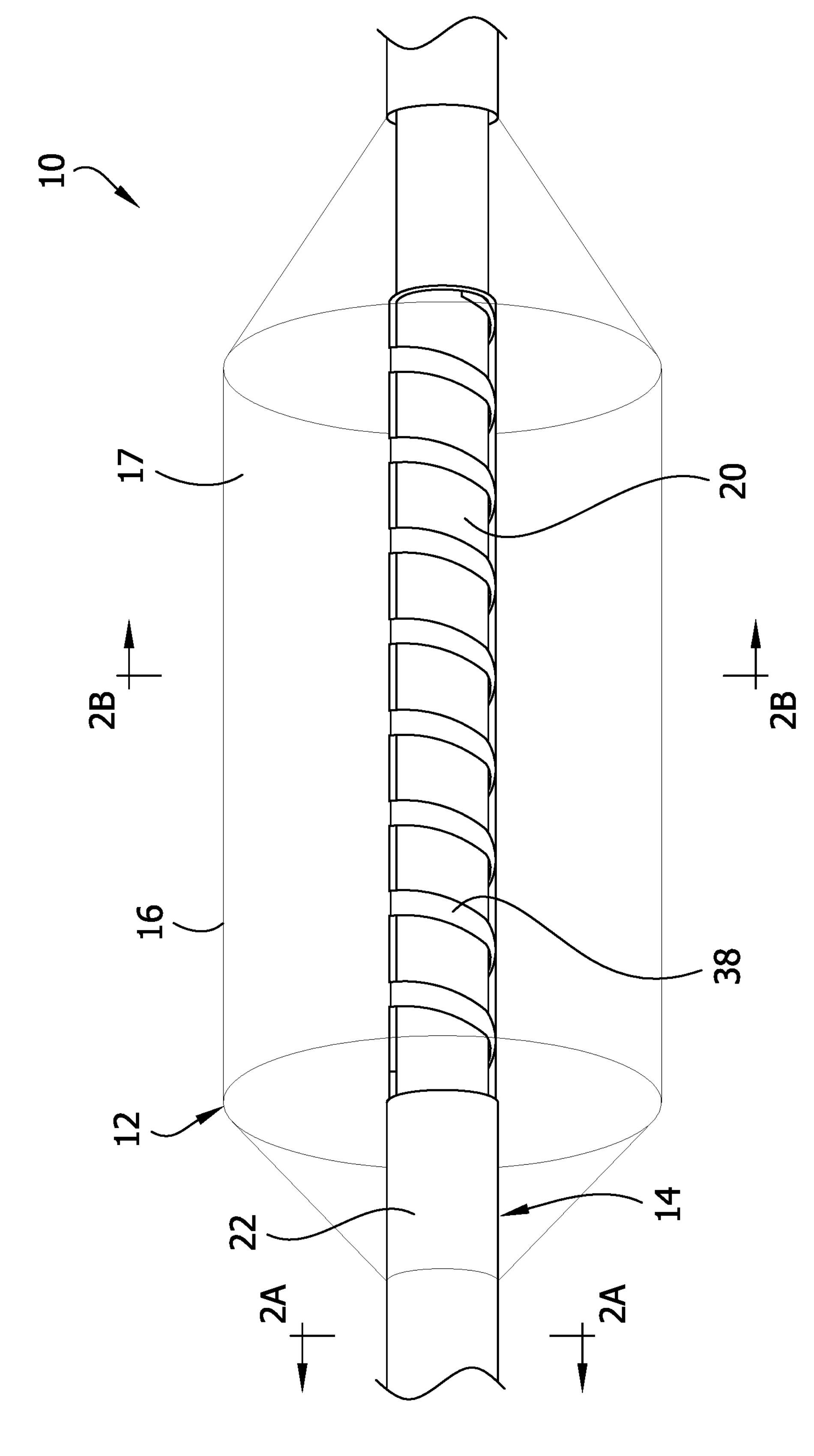
FIG. 1 is a fragmentary perspective of a balloon catheter.
Figure 2A:
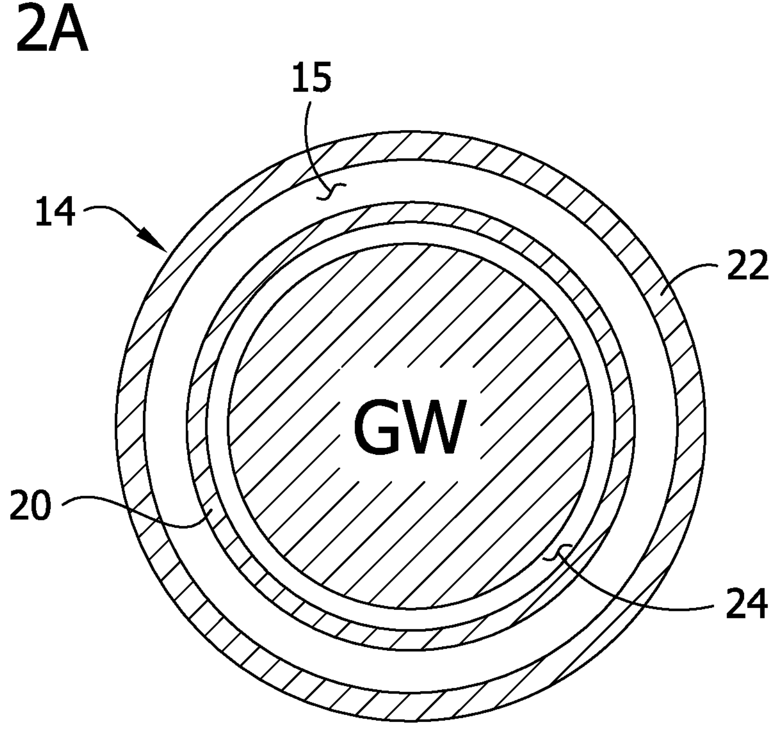
FIG. 2A is cross-section of the balloon catheter through line 2A-2A in FIG. 1.
Figure 2B:
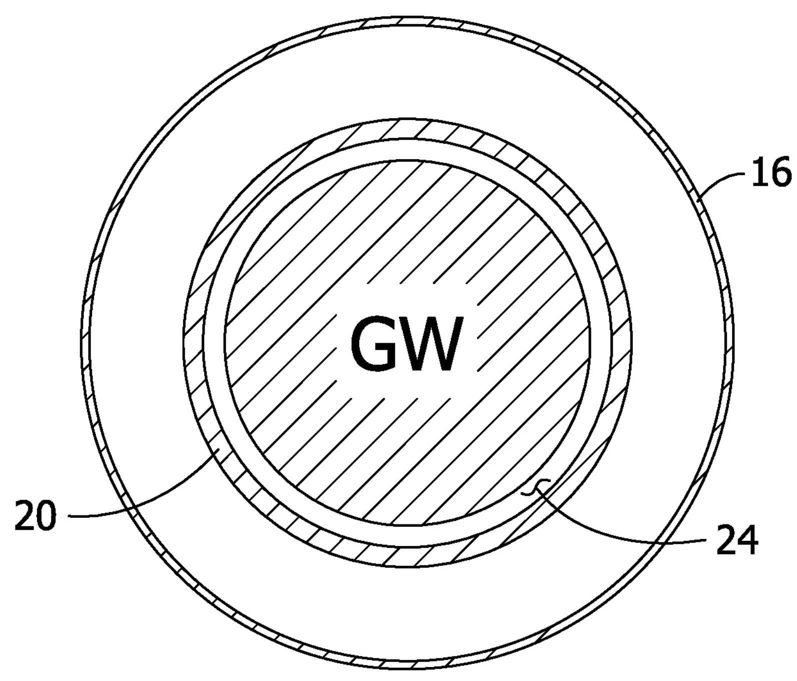
FIG. 2B is cross-section of the balloon catheter through line 2B-2B in FIG. 1.

Referring to FIGS. 1-2B, one embodiment of a balloon catheter is generally indicated at reference number 10. In general, the balloon catheter 10 comprises a medical balloon assembly, generally indicated at 12, and an inflation conduit assembly, generally indicated at 14. The inflation conduit assembly 14 defines an inflation lumen 15 and is fluidly coupled to the balloon assembly 12 to deliver inflation fluid through the inflation lumen to the interior of the balloon assembly. The balloon assembly 12 comprises at least one balloon 16. The balloon assembly 12 may include an additional number of balloons without departing from the scope of the disclosure. Each balloon may comprise one or more layers each having the same or different properties and constructions. The balloons 16 may be formed by any suitable manner such as from parisons or extrusion. As will be explained in greater detail below, inflation of the balloon 16 exerts pressure on the inside of the balloon, creating stress on the portion of the inflation conduit 14 extending through the balloon. In particular, the inflation conduit 14 experiences radial compression as a result of the pressure exerted by the inflated balloon. In conventional balloon catheters, the stresses on the inflation conduit can cause the inflation lumen to collapse preventing a guidewire from moving freely within the lumen.

In the illustrated embodiment, the balloon catheter 10 comprises a fully assembled balloon catheter that includes the medical balloon assembly 12, among other components. For example, the balloon catheter 10 may also comprise a stent (not shown) received around the deflated balloon assembly 12. It will be understood that a medical balloon assembly can comprise a subassembly of the balloon catheter. For example, in one or more embodiments, a balloon catheter 10 comprises the medical balloon assembly 12 in a subassembly separate from the inflation conduit 14.

In the illustrated embodiment, the balloon 16 comprises a single piece of monolithic material. For example, in one or more embodiments, the balloon 16 is formed from a bondable material, such as one of a PEBA and a nylon (e.g., one of PEBAX® elastomer and nylon 12). The balloon 16 can also have other configurations. For example, in one or more embodiments, one or more of the balloons of the balloon assembly can comprise a multi-layer balloon (e.g., co-extruded, multilayer balloon) or have other arrangements of sections of discrete materials. In certain embodiments, when the balloons are formed from multiple materials, portions (e.g., layers) of the balloon that contact the inflation conduit are formed from bondable materials such that the components of the medical balloon assembly can be secured by direct bonds.

The balloon 16 comprises a proximal neck defining the proximal end of the balloon and a distal neck defining the distal end of the balloon. A length of the balloon 16 extends along an axis of the balloon from the proximal end to the distal end thereof, and an inflatable portion 17 extends along the length of the balloon assembly between the proximal and distal necks. The inflatable portion 17 of the balloon 16 comprises a body, a proximal cone extending between the proximal neck and the body, and a distal cone extending between the distal neck and the body. When inflation fluid is delivered to the interior of the balloon 16 through the inflation conduit 14, the inflatable portion 17 is configured to radially expand from an uninflated configuration (not shown) to an inflated configuration (FIG. 1). Thus, the inflatable portion 17 defines an interior space of the balloon 16 when the balloon is inflated. In one or more embodiments, in the uninflated configuration of the balloon 16, the inflatable portion 17 comprises folds (e.g., wings) that are configured to wrap circumferentially around the balloon. The balloon can also have other arrangements in the uninflated configuration in certain embodiments. In one or more embodiments, the balloon 16 can be one of non-compliant, semi-compliant, and compliant in the inflated configuration. In the illustrated embodiment, the inflatable portion 17 of the balloon 16 has a generally cylindrical shape having conically tapered end segments in the inflated configuration. In one or more embodiments, the balloon 16 has other shapes in the inflated configuration.

Referring still to FIGS. 1-2B, the illustrated inflation conduit 14 is part of an elongate catheter body of the illustrated balloon catheter 10. The inflation conduit 14 has a proximal end portion configured for connection to an inflation fitting, a distal end portion secured to the balloon assembly 12, and a length extending along an axis of the inflation conduit from the proximal end portion to the distal end portion. Thus, the inflation conduit is connectable to a source of inflation fluid (not shown) for inflating the balloon 16. In one or more embodiments, the inflation lumen 15 extends from the proximal end portion to the distal end portion to provide fluid communication between the source of inflation fluid and the interior of the balloon assembly 12. The illustrated inflation conduit 14 comprises an inner inflation tube, generally indicated at reference numeral 20, and an outer inflation tube 22. The inflation lumen 15 is located radially between the inner inflation tube 20 and the outer inflation tube 22. In other embodiments, the inflation conduit 14 can have other configurations (e.g., the inflation conduit can comprise a single tube). In the illustrated embodiment, the inner inflation tube 20 functions as a guidewire tube defining a guidewire lumen 24. The guidewire lumen 24 is configured to slidably receive a guidewire GW therein such that the balloon catheter 10 can be advanced along a body lumen by sliding along a pre-placed guidewire.

Referring to FIGS. 3A-3B, the illustrated inner inflation tube 20 comprises a proximal portion 26, an intermediate portion 28 extending distally from the proximal portion, and a distal portion 30, extending distally from the intermediate portion. In one embodiment, the inner inflation tube 20 of the inflation conduit 14 comprises a three-layer construction including an inner layer 32, a tie layer 34 disposed around the inner layer, and an outer layer 36 disposed around the tie layer. The tie layer 34 is configured to bond the inner layer 32 to the outer layer 36. In one embodiment, the inner layer 32 comprises HDPE and the outer layer 36 comprises Pebax. The lubricious qualities of HDPE facilitate movement of the guidewire GW in the inner inflation tube 20. However, other materials could be used without departing from the scope of the disclosure. In other embodiments, the inner inflation tube 20 can have other configurations. For example, the inner inflation tube 20 can comprise a single layer tube. Additionally, a lubricious layer or coating may be disposed on an inner surface of the inner inflation tube 20 to facilitate guidewire delivery.

Referring to FIG. 1, at least one stiffener 38 is provided on or as part of the inner inflation tube 20 to reinforce the tube against compression forces exerted on the inflation conduit 14 when the balloon 16 is inflated. Thus, the stiffener 38 prevents the inner inflation tube 20 from being collapsed, or at least partially collapsed, under the pressure of the inflated balloon 16. Therefore, a condition of guidewire lock where the inner inflation tube 20 compresses around the guidewire GW preventing the guidewire from freely moving within the inner inflation tube is prevented. In one embodiment, the stiffener 38 is coextruded with outer layer 36 of the inflation tube 20. Coextruding the stiffener 38 allows the inner inflation tube 20 to maintain its outer diameter keeping the low profile configuration of the inner inflation tube. The stiffener 38 may comprise a stiffer polymer material than the outer layer 36 to reinforce the strength of the outer layer while still maintaining the flexibility of the inner inflation layer 20. For example, the stiffener 38 may comprise a stiffer Pebax material than the Pebax material of the outer layer 36. In one embodiment, the stiffener 38 comprises Pebax 72D. Still other polymer materials are envisioned. In the illustrated embodiment, the stiffener 38 comprises a polymer material extruded in a spiral configuration around the outer layer 36. Thus, a single continuous stiffener element 38 extends along the inner inflation tube 20. The spiral configuration allows the inner inflation tube 20 to maintain its flexibility while avoiding preferential bending in one direction/area. The spiral configuration of the stiffener 38 may have a constant pitch as illustrated, or the pitch may vary along an extension of the stiffener. It will be understood that reducing the pitch of the stiffener 38 will increase the relative stiffness of the inner inflation tube 20 at that particular location, and increasing the pitch of the stiffener will reduce the relative stiffness of the inner inflation tube at that particular location. The stiffener 38 may also have a constant width and/or thickness, or the width/thickness of the stiffener may vary along the length of the extrusion. In the illustrated embodiment, the stiffener 38 is located only in the distal portion 30 of the inner inflation tube 20. In particular, the stiffener 38 is located primarily within the inflation portion 17 of the balloon 16. However, the stiffener 38 could be located at other portions (i.e., intermediate portion 28 and proximal portion 26) without departing from the scope of the disclosure. Additionally, the stiffener 38 may be located in two or more sections of the inner inflation tube 20. Thus, the stiffener 38 may be located in all or at least two of the proximal portion 26, intermediate portion 28, and distal portion 30. Further, the stiffener 38 may be implemented in any application where it is desired to increase the strength of the guidewire lumen. This includes locations remote from the balloon, and in catheters that do not have balloons.

Referring to FIGS. 3A-3C, an outer diameter of the inner inflation tube 20 may also vary along a length L of the inner inflation tube which may alter the stiffness of the tube along its length. In one embodiment, the outer diameter of the inner inflation tube 20 tapers along at least a part of the intermediate portion 28 such that the proximal portion 26 has a larger outer diameter than the distal portion 30. An inner diameter of the inner inflation tube 20 may remain substantially constant along the length L of the inner inflation tube to facilitate receipt of the guidewire GW. Therefore, a thickness of the inner inflation tube 20 is greater along the proximal portion 26 than the distal portion 30. Thus, locating the stiffener 38 in the reduced thickness section of the distal portion 30 reinforces the distal portion equipping the distal portion to withstand the pressures exerted on the distal portion from the inflated balloon 16.

Figure 4:
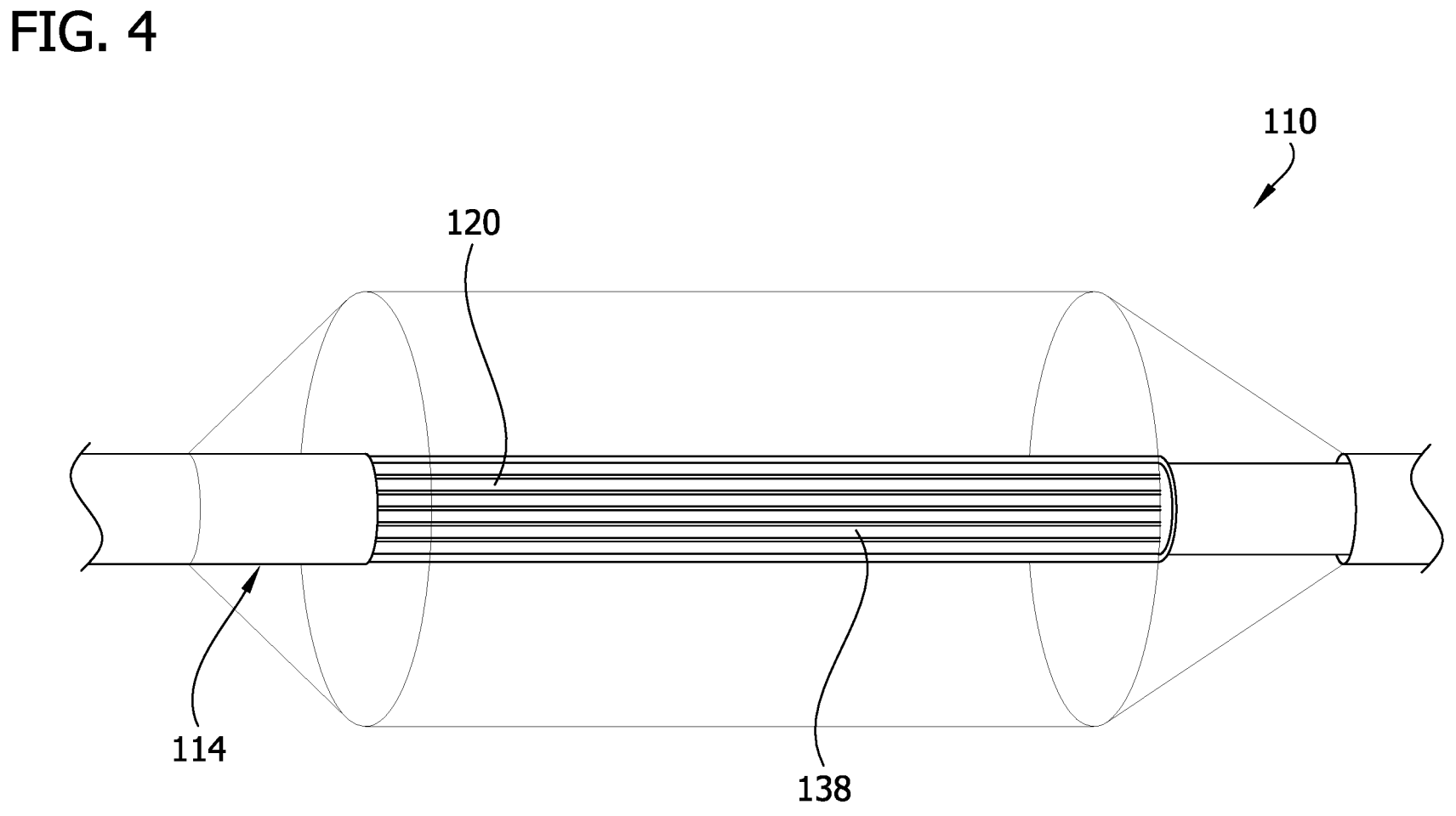
Figure 5:
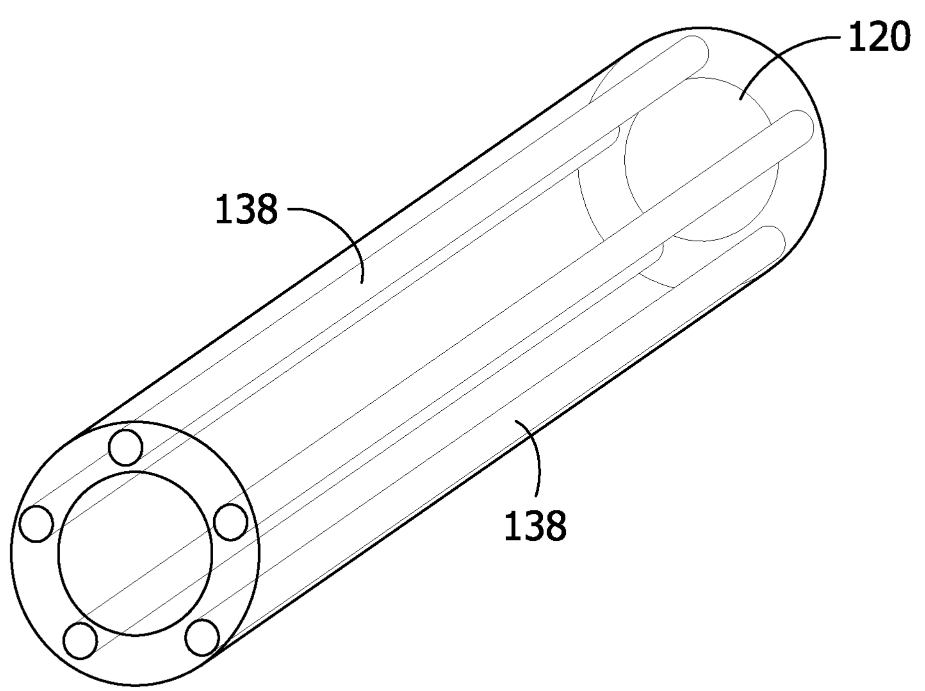
FIG. 5 is a fragmentary perspective of an inner inflation tube of the balloon catheter in FIG. 4.
Figure 6:
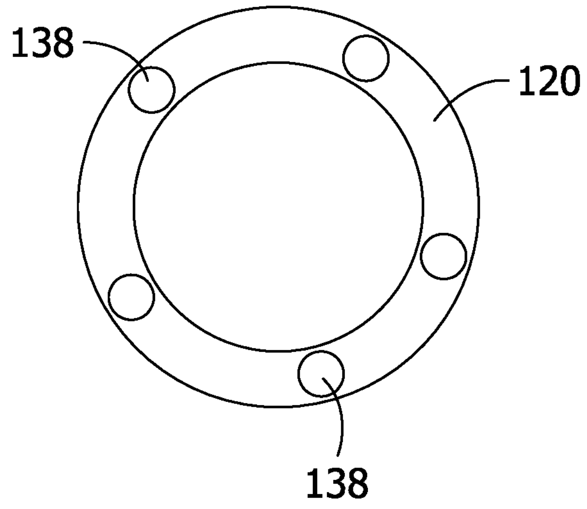
FIG. 6 is a cross-section of the inner inflation tube in FIG. 5.

Referring to FIGS. 4-6, another embodiment of a balloon catheter is generally indicated at 110. The balloon catheter 110 may comprise an inflation conduit 114 including an inner inflation tube 120 having stiffeners 138 that extend axially along a length of the inner inflation tube such that the stiffeners extend generally parallel to a longitudinal axis of the inner inflation tube. The stiffeners 138 are circumferentially spaced around the inner inflation tube 120. In the illustrated embodiment, there are five stiffeners 138 equally spaced around the circumference of the inner inflation tube 120. However, more or less stiffeners 138 having different spacing is envisioned without departing from the scope of the disclosure. The balloon catheter 110 is otherwise constructed and functions substantially the same as balloon catheter 10 of the previous embodiment.

Figure 7A:
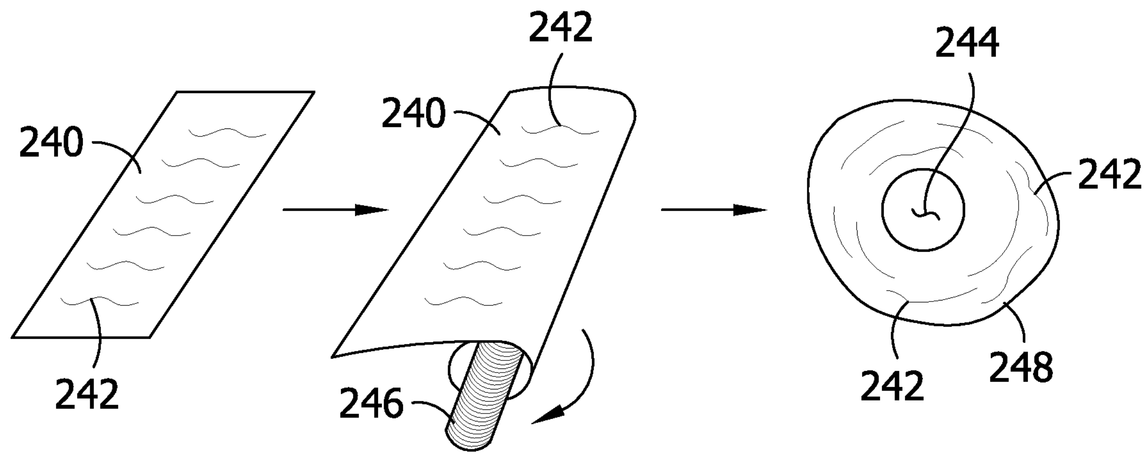
FIG. 7A is an illustration of a sheet rolling process for making a guidewire lumen.
Figure 7B:
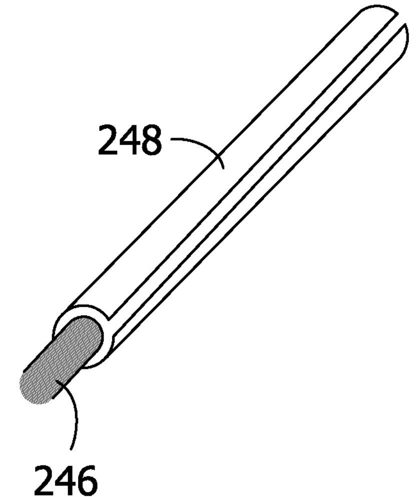
FIG. 7B is an illustration of a guidewire lumen made by the process in FIG. 7A.
Figure 7C:
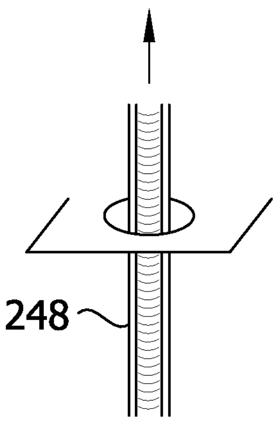
FIG. 7C is another illustration of a guidewire lumen made by the process in FIG. 7A.

Referring to FIGS. 7A-7C, an alternative method for forming a guidewire lumen is illustrated. A sheet of polymer 240 may be extruded such that molecules 242 (broadly, stiffeners) of the polymer generally extend in a common direction. In the illustrated embodiment, the molecules extend transverse to a longitudinal axis of the sheet 240. For example, the molecules 242 may extend generally orthogonal to the longitudinal axis of the sheet 240. A guidewire lumen 244 is created by rolling the sheet 240 around a mandrel 246 to form a tube 248 made from the sheet. The molecules 242 will then extend circumferentially around the guidewire lumen 244. This orientation of the molecules 242 increases the strength of the tube 248 against radial compression. Strengthening the tube 248 radially may also allow the device (e.g., catheter), apart which the tube is included, to maintain a low profile and/or increase the size of the guidewire lumen 244 without sacrificing the strength of the tube. Additionally, this configuration of the tube 248 creates a reinforced guidewire lumen 244 using only polymer materials. In one embodiment, edges of the sheet 240 are heat or laser bonded to seal the edges of the sheet forming the tube 248 (FIG. 7B). Applying heat to the tube 248 may also smooth out an inner surface of the tube to facilitate delivering a guidewire through the tube. The tube 248 could be formed by other means without departing from the scope of the disclosure. For instance, the edges of the sheet 240 could be laminated to form the tube 248 (FIG. 7C). Additionally, the construction of the tube 248 could be formed as part of a multilayer tube including the tube 248 as one of the layers. For example, the tube 248 could be formed as a top/outer layer of a three-layer tube including a middle tie layer and an inner layer (e.g., HDPE layer). Still other configurations of guidewire lumens including the rolled sheet 240 are envisioned.

Figure 8:
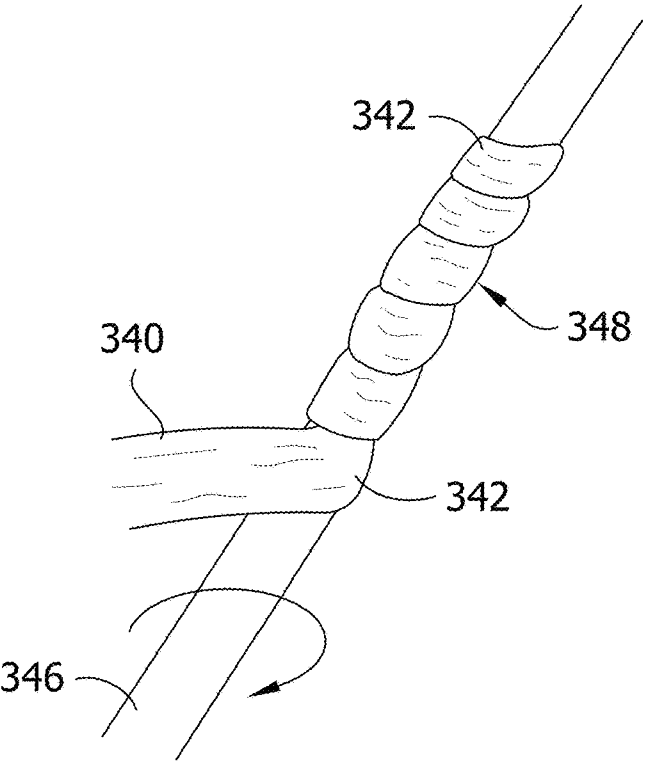
FIG. 8 is an illustration of a ribbon wrapping process for making a guidewire lumen of another embodiment.
Figure 9:
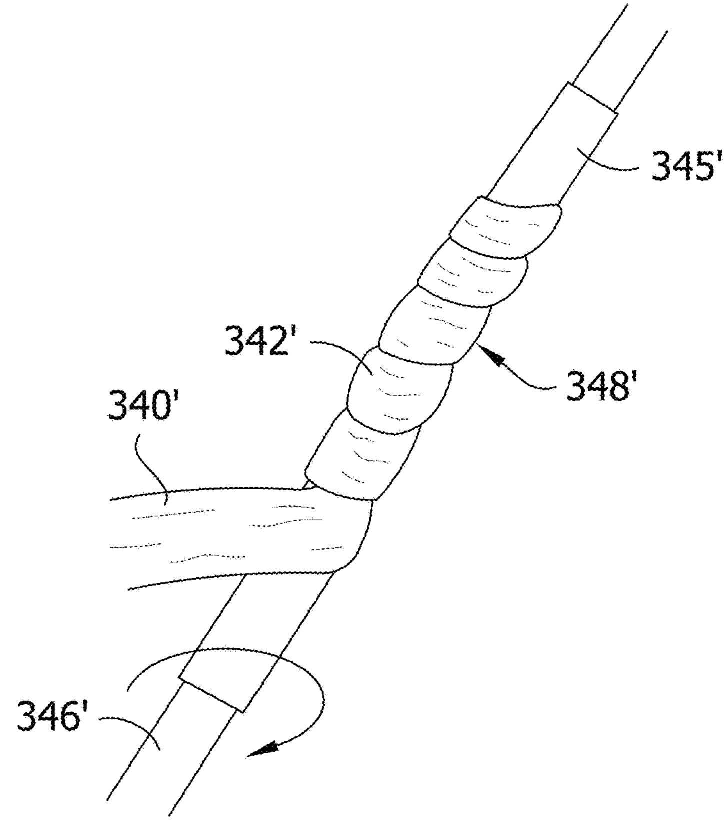
FIG. 9 is an illustration of a process of making a guidewire lumen of another embodiment.

Referring to FIG. 8, a ribbon of polymer material 340 could be extruded and wrapped around a mandrel 346 to form a tube 348 (e.g., catheter tube) defining a guidewire lumen. The ribbon 340 is extruded such that molecules 342 (broadly, stiffeners) of the material extend longitudinally along the extruded ribbon. In the illustrated embodiment, the ribbon 340 is then stretched longitudinally and wrapped in a spiral configuration around the mandrel 346 such that the molecules 342 of the material extend circumferentially around the tube 348. In one embodiment, the heat from extruding the ribbon of material 340 bonds the spiraled ribbon sections together forming the resulting tube 348. Alternatively, a heat shrink can be placed over the spiraled ribbon 340 and heated to bond the spiraled segments together to form the tube 348. The tube 348 alone can define the guidewire lumen or the ribbon or polymer material 340 could be wrapped around another tube to define the guidewire lumen. For example, a single or multi-layer tube may be used as a mandrel for the ribbon 340 to be wrapped around the tube to form a tube including both the single/multi-layer tube and the wrapped ribbon. Referring to FIG. 9, a ribbon of material 340' is wrapped around an inner liner 345' which is disposed around a mandrel 346'. In one embodiment, the inner liner 345' comprises a multi-layer tube. For example, the inner liner 345' may include an inner layer of HDPE and a tie layer disposed around the inner layer. The ribbon 340' is wrapped in a spiral configuration around the inner liner 345' and mandrel 346' such that molecules 342' (broadly, stiffeners) of the material extend circumferentially around the resulting tube 348' comprising the inner liner 345' and the wrapped ribbon 340'. The resulting tube is a tri-layer tube including the inner layer of HDPE, the middle tie layer, and the outer ribbon layer. Other tube configurations including the wrapped ribbon layer are envisioned without departing from the scope of the disclosure.

Figure 10:
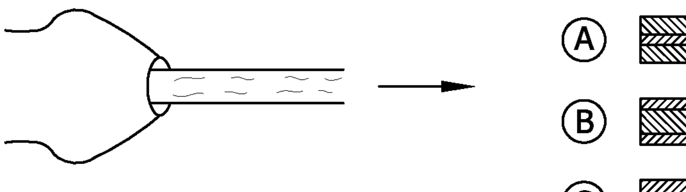
FIGS. 10 and 11 are illustrations of ribbons for forming a guidewire lumen.
Figure 11:
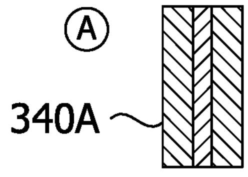
Figure 11:
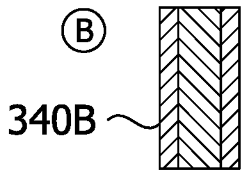
Figure 11:
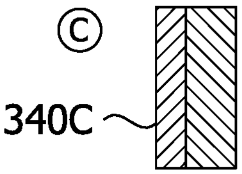
Figure 11:
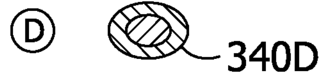
Figure 12:
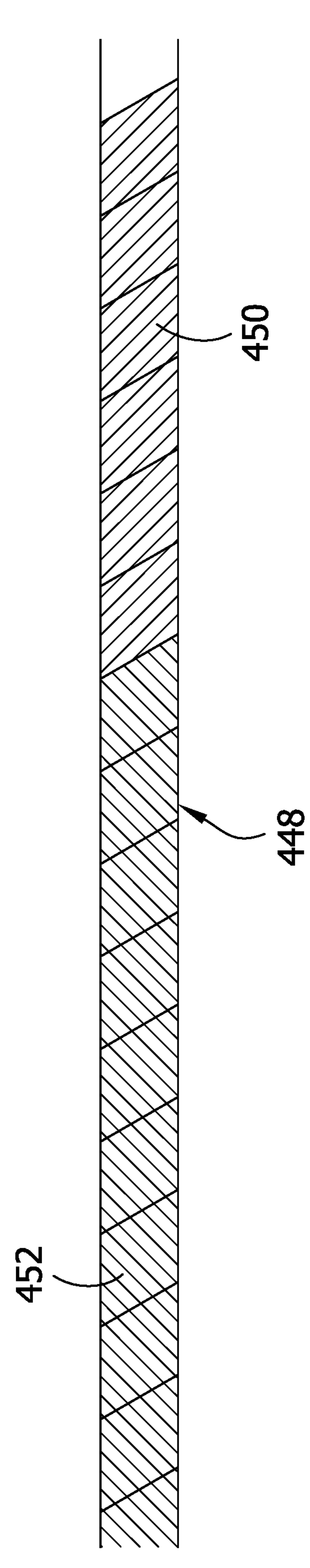
FIG. 12 is an illustration of a tube formed by ribbon wrapping.

In the illustrated embodiment, the ribbon of polymer material 340, 340' comprises a single polymer material. However, the ribbon of material could be formed from a plurality of different polymer materials. For example, polymer materials having different hardness levels could be extruded together to form a ribbon of polymer material comprising multiple polymers. Referring to FIGS. 10 and 11, in one embodiment, a ribbon of material 340A may include an inner longitudinally extending strip of harder polymer material and outer longitudinally extending strips of softer polymer material (FIGS. 10A and 11A). In one embodiment, a ribbon of material 340B may include an inner longitudinally extending strip of softer polymer material and outer longitudinally extending strips of harder polymer material (FIGS. 10B and 11B). In one embodiment, a ribbon of material 340C may include a first longitudinally extending strip of harder polymer material and a second, adjacent longitudinally extending strip of softer polymer material (FIGS. 10C and 11C). In one embodiment, a ribbon of material 340D may include a longitudinally extending strip of harder polymer material embedded within a longitudinally extending strip of softer polymer material (FIGS. 10D and 11D). The ribbons 340A-D when stretched and wrapped around a mandrel in a spiral configuration will produce a tube having alternating soft and hard sections spaced longitudinally along a length of the tube to provide strength to the tubing to resist radial compression while maintaining flexibility of the tube for traversing through the body. FIG. 12 illustrates a tube 448 having a relatively soft longitudinal section 450 formed from a softer polymer material, and a relatively hard longitudinal section 452 form from a harder polymer material. Still other configurations of polymer materials are envisioned. The ribbon may also include a polymer material and an additive included in the polymer material. For example, an additive improving the lubricity of the ribbon material could be added to the polymer material.

Modifications and variations of the disclosed embodiments are possible without departing from the scope of the invention defined in the appended claims.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A catheter comprising:

a catheter body having proximal and distal ends and including an inflation conduit having a length extending along a conduit axis between the proximal and distal ends of the catheter body;

an inflatable balloon coupled to the inflation conduit adjacent the distal end of the catheter body, wherein the inflation conduit includes an inner inflation tube including an inner tube body having an outer surface, an inner surface defining a guidewire lumen, a reinforced longitudinal portion, and a proximal longitudinal portion that is proximal of the reinforced longitudinal portion, and an extruded polymer material coupled to the outer surface of the reinforced longitudinal portion of the inner tube body, wherein substantially all molecules of the extruded polymer material are aligned and extend circumferentially around the outer surface of the inner tube body, and an outer inflation tube surrounding the inner inflation tube to define an annular inflation lumen between an inner surface of the outer inflation tube and the outer surface of the inner tube body, wherein the inflation lumen is in fluid communication with the inflatable balloon, wherein the reinforced longitudinal portion of the inner tube body is received in the inflatable balloon, wherein the reinforced longitudinal portion of the inner tube body has a thickness less than a thickness of the proximal longitudinal portion of the inner tube body, wherein the extruded polymer material strengthens the reinforced longitudinal portion of the inner tube body against radial compression forces imparted on the reinforced longitudinal portion by fluid pressure within the inflatable balloon when the inflatable balloon is being inflated, wherein the extruded polymer material comprises a ribbon of material wrapped around the reinforced longitudinal portion of the inner tube body, the ribbon including a first polymer layer formed from a first polymer material, a second polymer layer formed from a second polymer material, and a third polymer layer formed from a third polymer material, wherein the second polymer layer is sandwiched between the first and third polymer layers, wherein the first and second polymer materials have different hardnesses.

2. The catheter of claim 1, wherein the hardness of the first polymer material is greater than the hardness of the second polymer material.

3. The catheter of claim 1, wherein the inner tube body comprises multiple layers.

4. The catheter of claim 1, wherein the inner tube body consists of polymer materials.

5. The catheter of claim 1, wherein an entirety of the reinforced longitudinal portion is within the inflatable balloon.

6. The catheter of claim 1, wherein the inner tube body further includes a tie layer radially between the extruded polymer material and the inner tube body, wherein the tie layer couples the extruded polymer material to the inner tube body.

7. The catheter of claim 1, wherein the inner tube body comprises a polymer, wherein the extruded polymer material is stiffer than the polymer of the inner tube body.

8. The catheter of claim 1, wherein the extruded polymer material is in a spiral configuration around the outer surface of the inner tube body.

9. The catheter of claim 8, wherein the spiral configuration has a constant pitch.

10. The catheter of claim 1, wherein the hardness of the first polymer material is less than the hardness of the second polymer material.

11. A method of using the catheter of claim 1 comprising:

inserting a guidewire into the guidewire lumen; and inflating the inflatable balloon, wherein the reinforced longitudinal portion of the inner tube body resists radial compression due to the pressure exerted thereon by fluid pressure within the inflatable balloon as the inflatable balloon is inflated to enable the guidewire to move freely in the guidewire lumen.

* * * * *